United States Patent
Nakar et al.

(10) Patent No.: US 11,890,103 B2
(45) Date of Patent: Feb. 6, 2024

(54) IDENTIFYING ECG SIGNALS HAVING THE SAME MORPHOLOGY

(71) Applicant: Biosense Webster (Israel) Ltd., Yokneam (IL)

(72) Inventors: Elad Nakar, Timrat (IL); Amir Ben-Dor, Kibbutz Hamapil (IL); Noam Seker Gafni, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 168 days.

(21) Appl. No.: 17/523,244

(22) Filed: Nov. 10, 2021

(65) Prior Publication Data

US 2022/0061731 A1    Mar. 3, 2022

Related U.S. Application Data

(63) Continuation of application No. 16/550,594, filed on Aug. 26, 2019, now Pat. No. 11,213,240, which is a
(Continued)

(51) Int. Cl.
*A61B 5/35* (2021.01)
*A61B 5/00* (2006.01)
(Continued)

(52) U.S. Cl.
CPC ............... *A61B 5/35* (2021.01); *A61B 5/316* (2021.01); *A61B 5/361* (2021.01); *A61B 5/363* (2021.01);
(Continued)

(58) Field of Classification Search
CPC ........... A61B 5/35; A61B 5/316; A61B 5/361; A61B 5/363; A61B 5/364; A61B 5/366;
(Continued)

(56) References Cited

U.S. PATENT DOCUMENTS

| 5,000,189 A | 3/1991 | Throne |
| 2004/0243014 A1 | 12/2004 | Lee et al. |

(Continued)

FOREIGN PATENT DOCUMENTS

| EP | 2663227 B1 | 5/2021 |
| JP | 2008237882 A | 10/2008 |

(Continued)

OTHER PUBLICATIONS

European Search Report dated Dec. 11, 2017 from corresponding European Patent Application No. 17185489.6.
(Continued)

*Primary Examiner* — Paula J Stice
(74) *Attorney, Agent, or Firm* — Scully, Scott, Murphy & Presser, PC

(57) ABSTRACT

A method including processing electrocardiograph (ECG) signals taken over a heartbeat received over a plurality of channels, selecting a subset of the ECG signals captured at a point in time with a window of interest (WOI) around reference annotations and having a morphology pattern within the WOI, storing the morphology patterns, receiving continuous sets of ECG signals taken over a plurality of heartbeats over the plurality of channels and having a morphology pattern within the WOI, performing a correlation between the stored morphology patterns of the ECH signals and the morphology patterns of the continuous sets of ECH signals for each heartbeat, generating a correlation coefficient that is a measure of a goodness of fit between geometries of the ECG signals and the continuous sets of ECG signals and identifying each heartbeat having a correlation coefficient that exceeds a threshold coefficient as having been caused by an arrhythmia.

20 Claims, 6 Drawing Sheets

Related U.S. Application Data continuation of application No. 15/646,344, filed on Jul. 11, 2017, now Pat. No. 10,433,749.

(60) Provisional application No. 62/372,969, filed on Aug. 10, 2016.

(51) Int. Cl.
| | |
|---|---|
| A61B 5/316 | (2021.01) |
| A61B 5/361 | (2021.01) |
| A61B 5/363 | (2021.01) |
| A61B 5/364 | (2021.01) |
| A61B 5/366 | (2021.01) |
| A61B 5/287 | (2021.01) |

(52) U.S. Cl.
CPC .............. *A61B 5/364* (2021.01); *A61B 5/366* (2021.01); *A61B 5/7246* (2013.01); *A61B 5/287* (2021.01); *A61B 5/7264* (2013.01); *A61B 5/743* (2013.01); *A61B 2505/05* (2013.01)

(58) Field of Classification Search
CPC ..... A61B 5/7246; A61B 5/287; A61B 5/7264; A61B 5/743; A61B 2505/05
See application file for complete search history.

(56) References Cited

U.S. PATENT DOCUMENTS

| | | |
|---|---|---|
| 2012/0184858 A1 | 7/2012 | Harlev et al. |
| 2014/0005496 A1 | 1/2014 | Sison et al. |
| 2014/0276159 A1 | 9/2014 | Zhang |
| 2015/0057507 A1 | 2/2015 | Koyrakh et al. |

FOREIGN PATENT DOCUMENTS

| | | |
|---|---|---|
| JP | 2010516430 A | 5/2010 |
| JP | 2014503319 A | 2/2014 |

OTHER PUBLICATIONS

Office Action dated Oct. 2, 2018 from parent U.S. Appl. No. 15/646,344.
Office Action dated Mar. 22, 2019 from parent U.S. Appl. No. 15/646,344.
Notice of Allowance dated Jun. 5, 2019 from parent U.S. Appl. No. 15/646,344.
Office Action dated Jun. 9, 2021 from parent U.S. Appl. No. 16/550,594.
Notice of Allowance dated Aug. 26, 2021 from parent U.S. Appl. No. 16/550,594.

IDENTIFYING ECG SIGNALS HAVING THE SAME MORPHOLOGY

CROSS-REFERENCE TO RELATED APPLICATION

This application is a continuation application of U.S. Ser. No. 16/550,594 filed on Aug. 26, 2019, now U.S. Pat. No. 11,213,240 granted on Jan. 4, 2022 which is a continuation of Ser. No. 15/646,344 filed on Jul. 11, 2017, now U.S. Pat. No. 10,433,749 granted on Oct. 8, 2019 which claims the benefit of U.S. Provisional Patent Application 62/372,969, filed Aug. 10, 2016, which are incorporated herein by reference.

FIELD OF THE INVENTION

This invention relates generally to electrocardiograph (ECG) signals, and specifically to detecting ECG signals having similar morphologies.

BACKGROUND OF THE INVENTION

For correctly mapping regions of a heart chamber which generate an arrhythmia, it is essential that only signals, or beats, exhibiting that specific arrhythmia are captured. Signals from effects such as ectopic beats, mechanical stimulation of the tissue, and arrhythmia changes in morphology due to alternative activation patterns with the same cycle length, should be ignored. Introducing results from such signals into a map will cause inaccuracies in the local activation map, and the deformed visualization of the arrhythmia makes it difficult to clearly identify the arrhythmia mechanisms.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

In one embodiment a method, includes processing a first set of electrocardiograph (ECG) signals taken over a single heartbeat of a human subject, the first set of ECG signals being received over a plurality of channels; receiving reference annotations of the first set of ECG signals; selecting a subset of the first set of ECG signals captured at a point in time with a window of interest (WOI) around the reference annotations of the first set of ECG signals, the subset of signals each having a morphology pattern within the WOI; storing the morphology patterns of the subset of ECG signals; receiving continuous sets of ECG signals taken over a plurality of heartbeats of a human subject, the continuous sets of ECG signals being received over the plurality of channels, each of the continuous sets of ECG signals having a morphology pattern within the WOI for each heartbeat; performing a correlation between the stored morphology patterns of the first set of ECH signals and the morphology patterns of each of the continuous sets of ECH signals for each heartbeat; generating for each heartbeat of the plurality of heartbeats a correlation coefficient that is a measure of a goodness of fit between geometries of the first set of ECG signals and each of the continuous sets of ECG signals; and identifying each heartbeat of the plurality of heartbeats having a correlation coefficient that exceeds a threshold coefficient as having been caused by an arrhythmia.

In some embodiments the reference annotations correspond to a time of occurrence of a largest positive value on one selected ECG signal, a largest negative value on one selected ECG signal, a largest positive slope on one selected ECG signal or a largest negative slope on one selected ECG signal. In some embodiments the time of occurrence corresponds to a time of activation of a section of myocardium generating the ECG signals. In some embodiments a weighted correlation score is calculated over all the channels, for each heartbeat. In some embodiments a location of the identified heartbeat is incorporated into a map of the heart generating the ECG signals. Some embodiments include applying a phase shift between the first set of ECG signals and the continuous sets of ECG signals prior to generating the correlation coefficient. Some embodiments include iteratively altering the phase shift to determine a maximum weighted correlation coefficient, and identifying each heartbeat of the plurality of heartbeats having a maximum weighted correlation coefficient that exceeds the threshold coefficient as having been caused by an arrhythmia.

There is further provided, according to an embodiment an apparatus, including a set of electrodes configured to be positioned in a heart of a human subject for acquiring electrocardiograph (ECG) signals over a plurality of channels; and a processor, configured for: processing a first set of electrocardiograph (ECG) signals taken over a single heartbeat of a human subject; receiving reference annotations of the first set of ECG signals; selecting a subset of the first set of ECG signals captured at a point in time with a window of interest (WOI) around the reference annotations of the first set of ECG signals, the subset of signals each having a morphology pattern within the WOI; storing the morphology patterns of the subset of ECG signals; receiving continuous sets of ECG signals taken over a plurality of heartbeats of a human subject, the continuous sets of ECG signals being received over the plurality of channels, each of the continuous sets of ECG signals having a morphology pattern within the WOI for each heartbeat; performing a correlation between the stored morphology patterns of the first set of ECH signals and the morphology patterns of each of the continuous sets of ECH signals for each heartbeat; generating for each heartbeat of the plurality of heartbeats a correlation coefficient that is a measure of a goodness of fit between geometries of the first set of ECG signals and each of the continuous sets of ECG signals; and identifying each heartbeat of the plurality of heartbeats having a correlation coefficient that exceeds a threshold coefficient as having been caused by an arrhythmia.

The present disclosure will be more fully understood from the following detailed description of the embodiments thereof, taken together with the drawings, in which:

DETAILED DESCRIPTION OF EMBODIMENTS

Overview

Embodiments of the present invention provide an ECG morphology matching algorithm which aims to identify all beats representing the same morphology in ECG signals. The algorithm is compatible with body surface (BS) (typically 12 leads) signals and/or intra-cardiac (IC) signals. The algorithm receives a morphology pattern of ECG signals as an input and searches for the same morphology in continuous ECG signals.

A user of the present invention selects the input morphology pattern by defining a window of interest (WOI) around a specific annotation, The algorithm compares the morphology of the selected pattern with the morphology of incoming ECG signals. Beats that are within a predetermined weighted correlation threshold are considered to represent the same morphology. The algorithm operates in real-time, as beat signals are acquired by a probe in the heart.

By using the results of the algorithm, regions of the heart that are the source of the matched beats may be indicated automatically on a map of the heart.

An embodiment of the present invention provides a method, comprising selecting an initial set of electrocardiograph (ECG) signals taken over a single heartbeat of a human subject, the set having respective morphologies to be used as a template for an arrhythmia of the subject, and receiving a subsequent set of ECG signals taken over a subsequent heartbeat of the human subject. The method further comprises performing a cross-correlation between the initial set and the subsequent set, so as to generate a correlation coefficient that is a measure of a goodness of fit between geometries of the initial set and the subsequent set. When the correlation coefficient exceeds a threshold coefficient, the subsequent heartbeat is accepted as having been caused by the arrhythmia.

DESCRIPTION OF EMBODIMENTS

Figure 1:
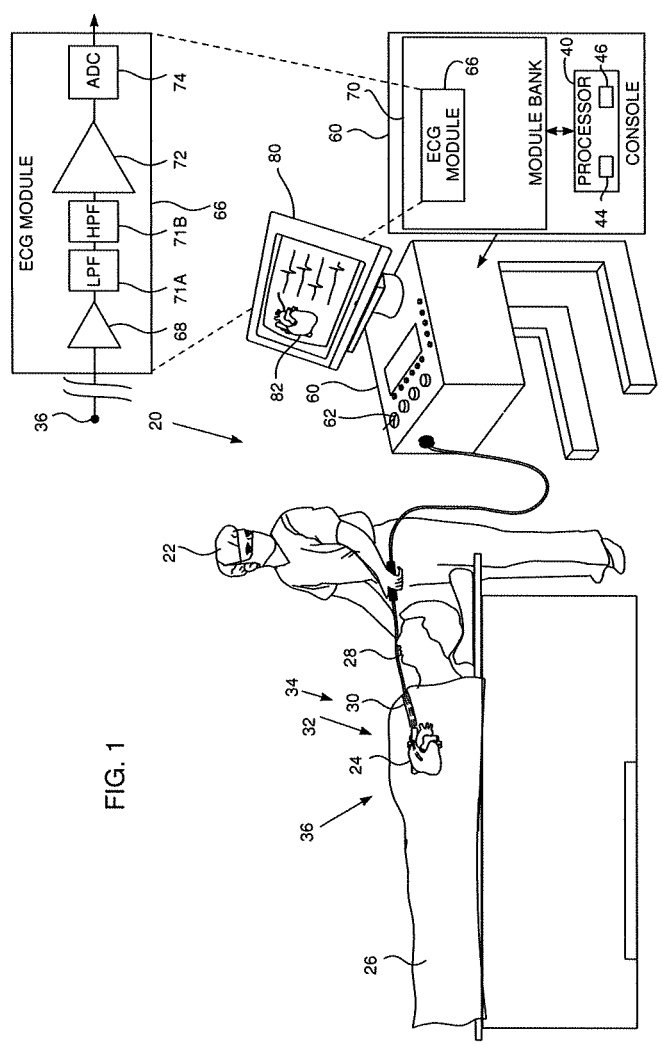
FIG. 1 is a schematic illustration of an invasive medical procedure, according to an embodiment of the present invention.

FIG. 1 is a schematic illustration of an invasive medical procedure using an apparatus 20, according to an embodiment of the present invention. The procedure is performed by a medical professional 22, and, by way of example, the procedure in the description hereinbelow is assumed to comprise acquisition of intra-cardiac electrocardiogram (IC ECG) signals from a heart 24 of a human patient 26. While embodiments of the present invention analyze either IC ECG or BS (body surface) ECG signals, for simplicity and clarity the following description, except where otherwise stated, assumes that IC ECG signals are analyzed.

In order to acquire the IC ECG signals, professional 22 inserts a probe 28 into a sheath 30 that has been pre-positioned in a lumen of the patient. Sheath 30 is positioned so that a distal end 32 of the probe may enter the heart of the patient, after exiting a distal end 34 of the sheath, and contact tissue of the heart.

Probe 28 may comprise any type of catheter that can be inserted into the heart of the patient, and that can be tracked, typically using a magnetic tracking system and/or an impedance measuring system. For example, probe 28 may comprise a lasso catheter, a shaft-like catheter, or a pentaRay catheter, produced by Biosense Webster of Diamond Bar, CA, or catheters generally similar to these catheters. Biosense Webster also produces a magnetic tracking system and an impedance measuring system that may be used in embodiments of the present invention.

Probe 28 comprises one or more electrodes 36, which are used to acquire the ECG signals used by a processor 40, comprised in apparatus 20, in performing the algorithms described herein. Processor 40, in addition to acting as a central processing unit, may comprise real-time noise reduction circuitry 44, typically configured as a field programmable gate array (FPGA), followed by an analog-to-digital (A/D) signal conversion integrated circuit 46. The processor can pass the signal from A/D circuit 46 to another processor and can be programmed to perform the algorithms disclosed herein.

Processor 40 is located in an operating console 60 of the apparatus. Console 60 comprises controls 62 which are used by professional 22 to communicate with the processor. During the procedure, processor 40 communicates with an ECG module 66 in a module bank 70, in order to acquire ECG signals as well as to perform the algorithms disclosed herein.

ECG module 66 receives ECG signals from electrode 36. In one embodiment the signals are transferred, in module 66, through a low noise pre-amplifier 68, and via low pass and high pass filters 71A, 71B, to a main amplifier 72. Module 436 also comprises an analog to digital converter (ADC) 74, which transfers digitized values of the ECG signals to processor 40, for implementation by the processor of the algorithms described herein. Typically, processor 40 controls the operation of pre-amplifier 68, filters 71A, 71B, amplifier 72, and ADC 74.

For simplicity FIG. 1 illustrates ECG module 66 as having one channel for receiving signals from electrode 36. However, it will be understood that the module typically comprises multiple channels substantially similar to that shown. For example, module 66 may comprise 12 such channels, which may be used to receive signals from 12 body surface electrodes.

ECG module 66 enables processor 40 to acquire and analyze EP (electrophysiological) signals received by electrode 36, including the ECG signals referred to herein. The signals are typically presented to professional 22 as voltage-time graphs, which are updated in real time, on a display screen 80.

The software for processor 40 and module bank 70 may be downloaded to the processor in electronic form, over a network, for example. Alternatively or additionally, the software may be provided on non-transitory tangible media, such as optical, magnetic, or electronic storage media.

In order to operate apparatus 20, module bank 70 typically comprises modules other than the ECG module described above, such as one or more tracking modules allowing the processor to track the distal end of probe 28. For simplicity, such other modules are not illustrated in FIG. 1. All modules may comprise hardware as well as software elements.

In addition to display screen 80 presenting ECG signals acquired by electrode 411, results of the algorithms described herein may also be presented to the algorithm user on the display screen. For example, the results may be incorporated into a map 82 of heart 24.

Figure 2:
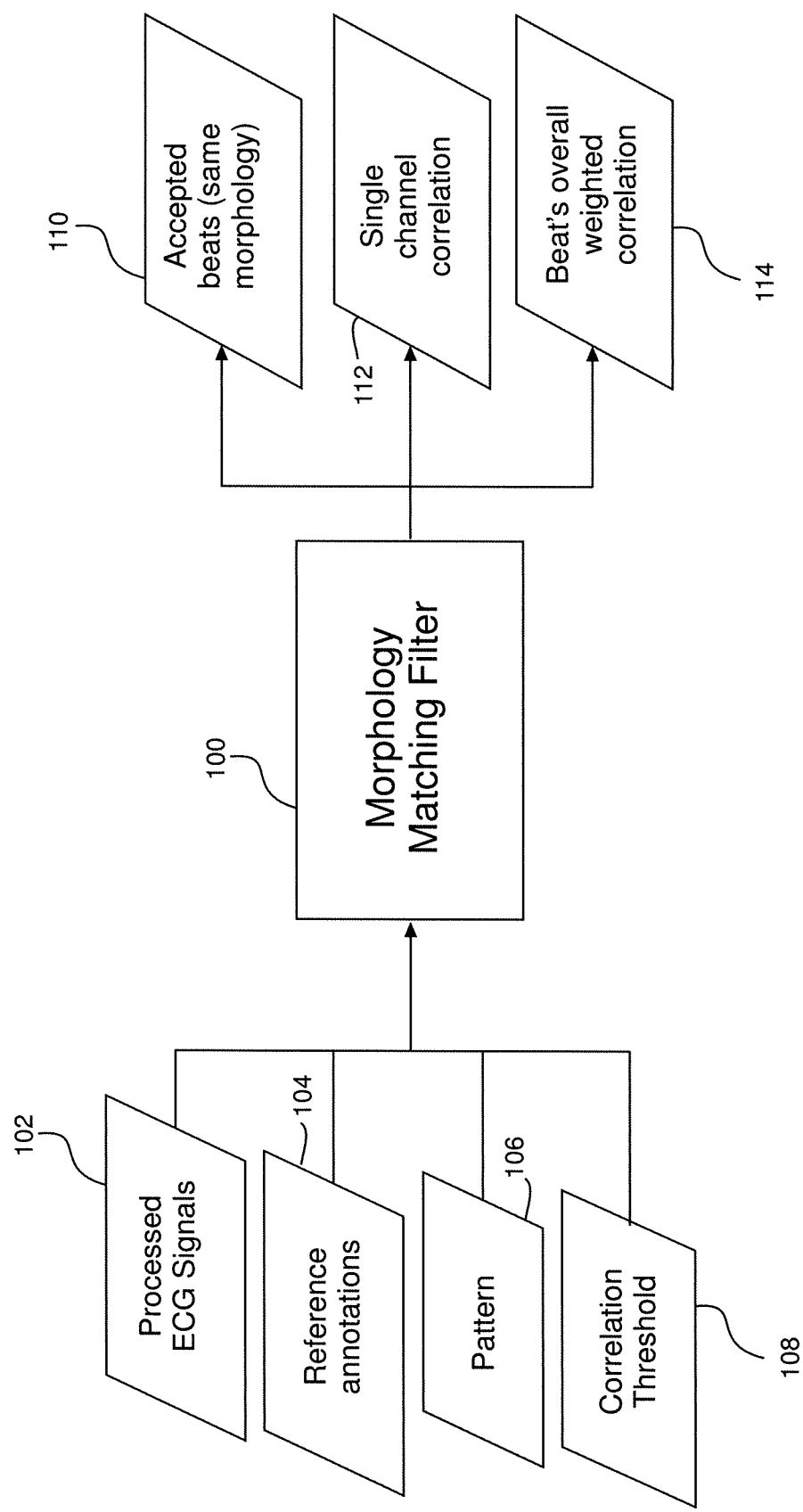
FIG. 2 is a schematic block diagram illustrating inputs and outputs of an ECG morphology matching algorithm, according to an embodiment of the present invention.

FIG. 2 is a schematic block diagram illustrating inputs and outputs of an ECG morphology matching algorithm, according to an embodiment of the present invention. The algorithm is implemented by processor 40, and acts as a morphology matching filter 100 which accepts as inputs:

A set 102 of ECG signals which have been processed as described above, by multiple channels of ECG module 66.

Reference annotations 104 of the signals, computed by processor 40. An annotation of a signal is an assumed time of occurrence of the signal. In one embodiment the annotation corresponds to the time of occurrence of the largest positive value on one selected ECG signal. Several criteria options exist for the reference annotation (positive value, negative value, largest negative slope, largest positive slope) and for IC ECG signals the time of occurrence typically corresponds to the time of activation of the section of myocardium generating the signal. Criteria for choosing the ECG signal for annotations, corresponding to that described above or other criteria, may be defined by professional 22. The professional also selects the ECG channels to be used to acquire the signals being analyzed. For BS ECG signals there are typically 12 channels; for IC ECG signals the number of channels corresponds to the number of electrodes 36 being used.

A morphology pattern 106. This is a set of ECG signals that is selected by professional 22, and that is captured at a specific point in time, with a window of interest (WOI) around annotations of the signals that are defined by the professional. The WOI defines the time period for the morphology matching algorithm. Morphology pattern 106 acts as a template against which other ECG signals are compared, and the pattern may also be referred to herein as a template.

A correlation threshold 108, set by professional 22, to be used by the algorithm in deciding if a beat matches the morphology pattern.

Outputs of the algorithm are:

A beat status 110. I.e., an accepted beat having the same morphology as the input morphology pattern 106, or a rejected beat having a different morphology from the input pattern. In one embodiment a location of an accepted beat is incorporated into a map of the heart generating the ECG signals.

A correlation score 112 for each channel of set 102 of signals (in some embodiments these scores may not be presented to professional 22).

A weighted correlation score 114, calculated over all the channels, for each beat.

Figure 3:
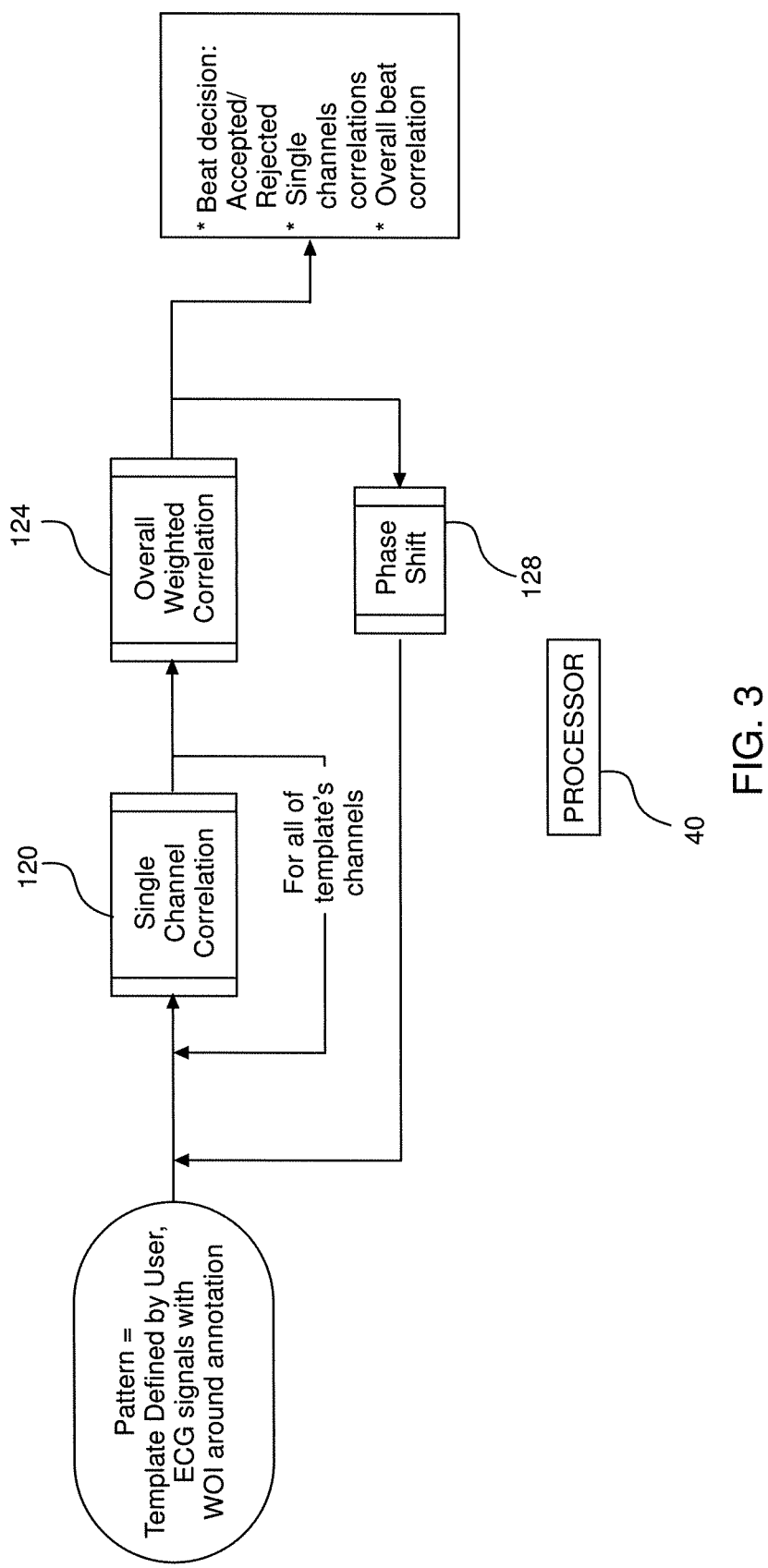
FIG. 3 is a schematic block diagram illustrating the ECG morphology matching algorithm, according to an embodiment of the present invention.
Figure 4:
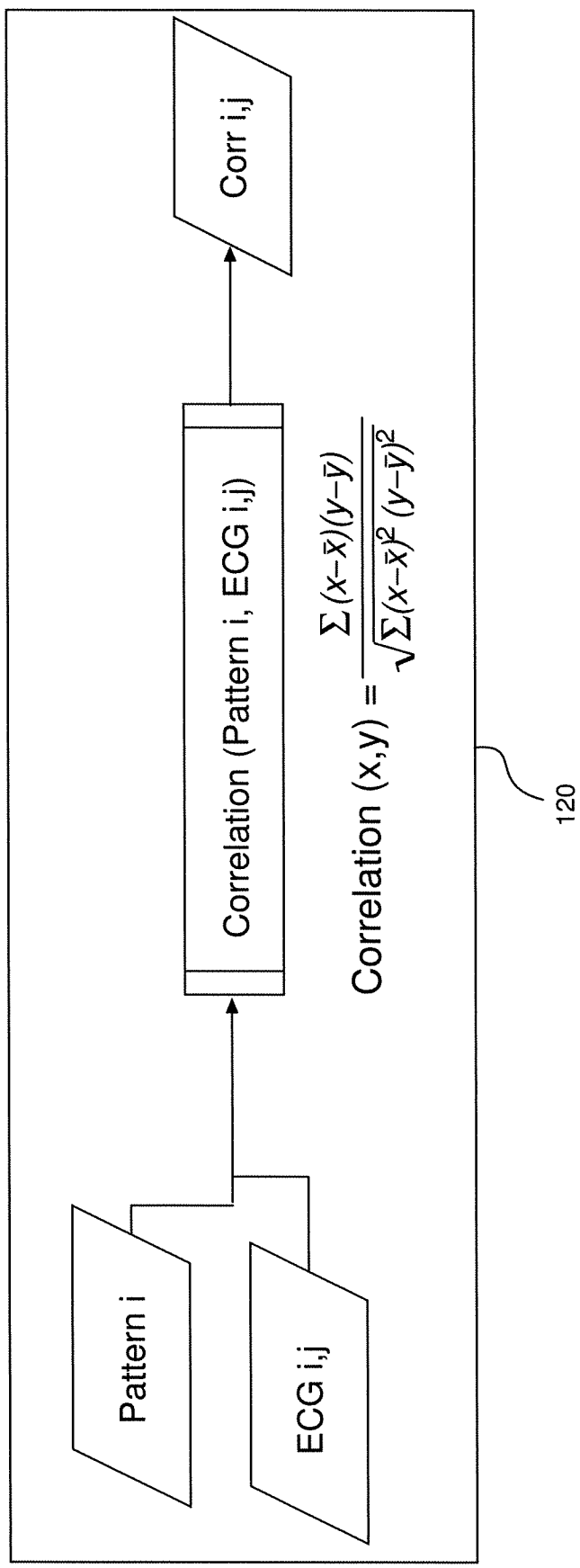
FIGS. 4, 5, and 6 are schematic diagrams illustrating operations of blocks of the algorithm, according to an embodiment of the present invention.
Figure 5:
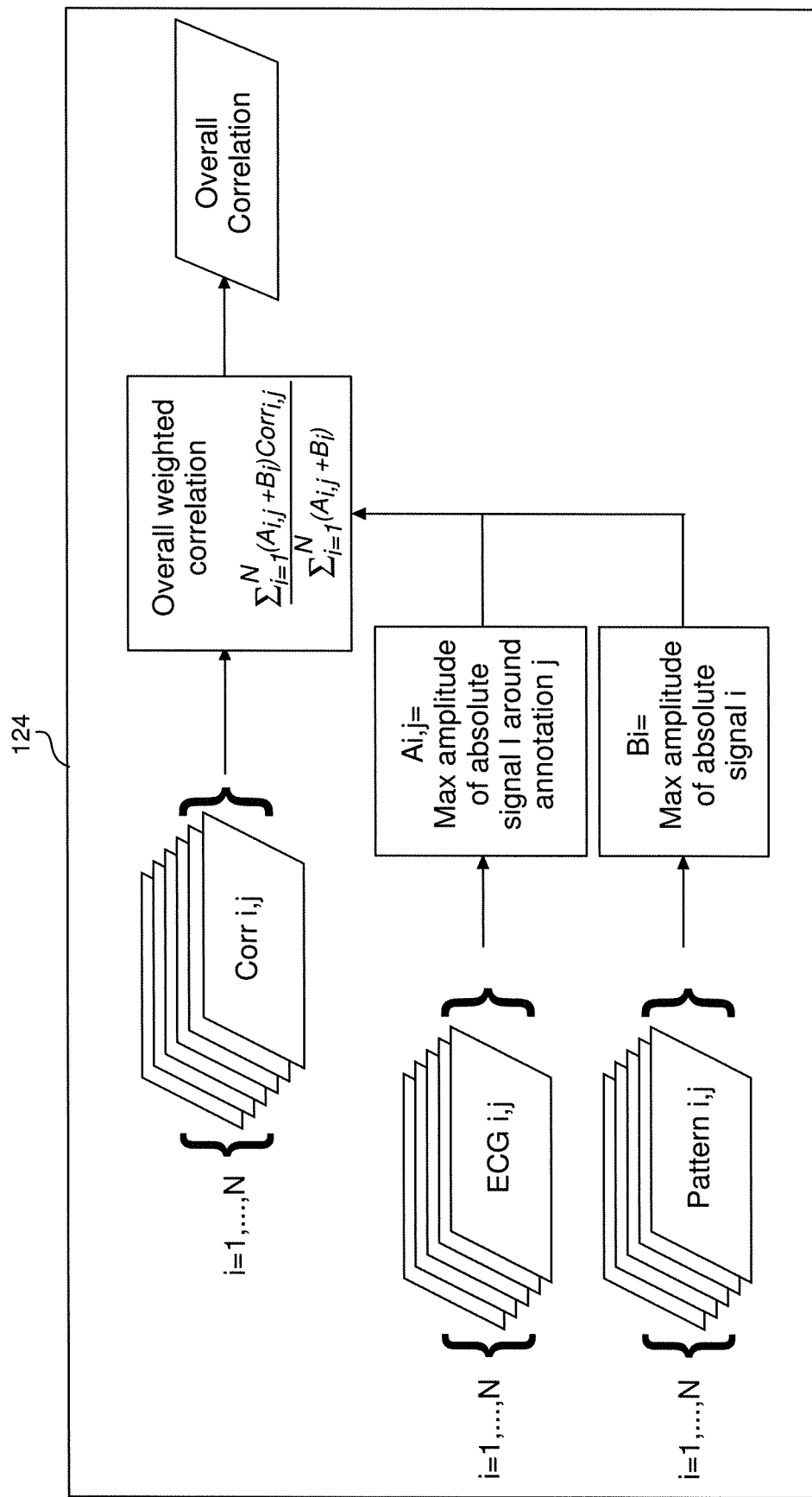
Figure 6:
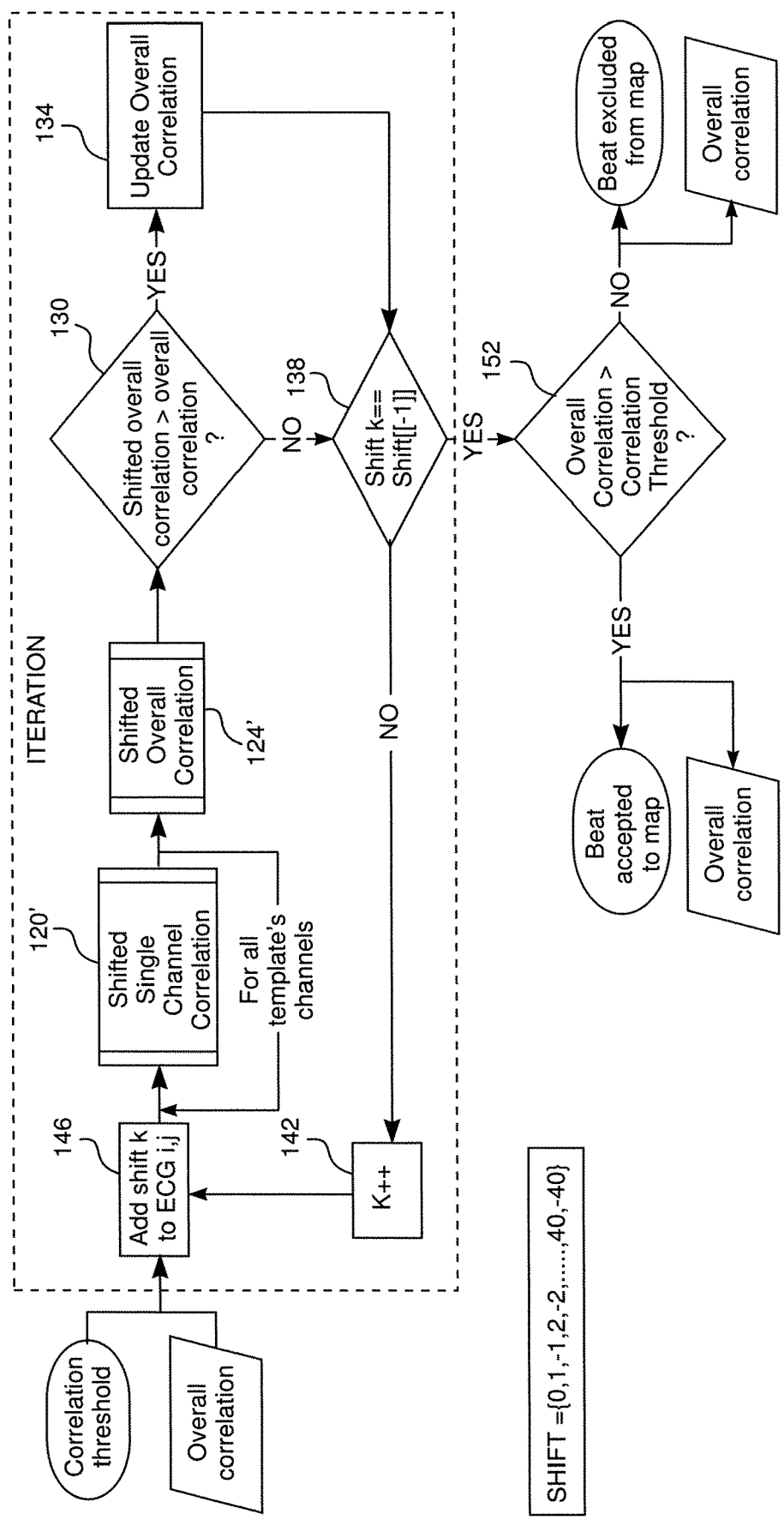

FIG. 3 is a schematic block diagram illustrating the ECG morphology matching algorithm, and FIGS. 4, 5, and 6 are schematic diagrams illustrating operations of blocks of the algorithm, according to an embodiment of the present invention. By way of example processor 40 is assumed to operate the algorithm. In other embodiments the processor may be a stand-alone processor, and/or a general purpose processor that is typically operating a computer.

In a first step of the algorithm, corresponding to the "single Channel Correlation" block 120, the processor performs a correlation, with stored morphology pattern 106, within the WOI period as defined by professional 22, for every channel of an incoming beat. FIG. 4 illustrates how the correlation is performed. As shown in FIG. 4, the processor uses as inputs:

Morphology pattern 106 (Pattern i) described above with reference to FIG. 2.

An ECG signal to be tested (ECG i,j). The signal to be tested has a WOI temporal width corresponding to the WOI width of the morphology pattern defined by professional 22. The temporal position of the WOI is selected to include a real-time annotation, calculated by the processor, of the signal.

i is a numerical index defining the channel of the pattern (typically, for BS ECG, i=1, 2, ... 12), and j is a numerical index defining a position of an annotation of the ECG signal.

The processor calculates, for each channel, a correlation coefficient according to the following equation:

$$\text{Correlation}(x, y) = \frac{\sum_k (x - \bar{x})(y - \bar{y})}{\sqrt{\sum_k (x - \bar{x})^2 (y - \bar{y})^2}} \quad (1)$$

where
x is the sample value of the template reference ECG data,
$\bar{x}$ is the average value of the template reference ECG data,
y is the sample value of the current beat ECG data being tested,
$\bar{y}$ is the average value of the current beat ECG data being tested, and
k is a numerical index defining which data sample of the ECG signal is being analyzed. For example, if the WOI is for 120 msec, from −50 msec (before the reference annotation) to +70 msec (after the reference annotation), and we sample every msec, then k is a set of 120 values for the 120 samples.

It will be understood that the correlation performed by equation (1) compares the geometries, or shapes, of the template reference ECG data with the current beat ECG data. A high value of Correlation (x,y), i.e., close to unity, means that the two geometries, of the template and of the current beat, are similar.

In a second step of the algorithm, corresponding to an "Overall Weighted Correlation" block 124 of FIG. 3, the processor calculates an overall correlation, for a specific beat, using the values of the correlation coefficient calculated in the first step, i.e., according to equation (1).

FIG. 5 illustrates how the correlation is performed. As shown in FIG. 5, the processor uses as inputs:

The correlation score, i.e., the output of equation (1) for each channel of a beat being tested. The beat being tested is the ECG signal (of the particular channel) which is in a WOI around a current annotation.

The ECG signal (beat) being tested.

The morphology pattern (Pattern i) described above with reference to FIG. 1.

Also as shown in FIG. 5, the processor calculates an absolute maximum amplitude Ai,j of the ECG signal being tested, and an absolute maximum amplitude Bi of the morphology pattern.

The processor uses the sum of Ai,j and Bi as weights to calculate an overall correlation according to equation (2):

$$\text{Overall Correlation} = \frac{\sum_{i=1}^{N}(A_{i,j} + B_i)\text{Corr}_{i,j}}{\sum_{i=1}^{N}(A_{i,j} + B_i)} \quad (2)$$

Where Corri,j is the correlation coefficient calculated by equation (1), and N is the number of ECG channels being analyzed. In the case of BS signals, N is typically 12.

The overall correlation coefficient calculated by equation (2) depends on the phase of the ECG signal being tested relative to the phase of the morphology pattern.

In a third step of the algorithm, corresponding to a "Phase Shift" block 128 of FIG. 3, the processor iteratively changes the phase, of the ECG signal being tested, relative to the phase of the morphology pattern. The processor uses as inputs:

The value of the overall correlation from equation (2).
The correlation threshold 108 (FIG. 2) as set by professional 22. The threshold may be between 0 and 1, and a typical value is 0.9.

FIG. 6 explains, in an iteration set of blocks, the iterative process performed by single channel correlation block 120, overall weighted correlation block 124, and phase shift block 128. As shown in FIG. 6, at each iteration, the processor repeats the first two steps described above, in a "shifted single channel correlation" block 120' and a "shifted overall correlation" Block 124'. During the iterations the processor determines a maximum value of the overall correlation as the result of equation (2).

FIG. 6 illustrates that phase shift iterations are performed every 1 msec in a ±40 msec time frame measured from the annotation of the beat being analyzed. An index k defines the phase shift being evaluated, and k={−40, . . . 0, . . . +40}. At each iteration the value of the shifted overall correlation is compared to a previous maximum correlation in a comparison block 130, and if comparison 130 returns positive the overall correlation is updated in an update block 134.

If the return is negative control continues to a comparison block 138, which checks if there are any more values of index k to be iterated. If there are, k is incremented in an incremental block 142, the new value of k is applied to the ECG signal in a signal block 146, and the flowchart returns to block 120'.

If the iterations have completed, then control continues to a final comparison block 152, where the output of the iteration set of blocks, the maximum value of the overall correlation that is in block 134 is compared to the input threshold value. If the comparison returns positive, the beat is assumed to represent the same arrhythmia as the morphology pattern. In this case processor 40 may add this beat information into collective information of map 82 of the heart (FIG. 1). If the comparison returns negative, the beat is assumed to represent a different arrhythmia from the morphology pattern, and therefore the information is not added to the map collective information.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
processing a first set of electrocardiograph (ECG) signals taken over a single heartbeat of a human subject, the first set of ECG signals being received over a plurality of channels;
receiving reference annotations of the first set of ECG signals;
selecting a subset of the first set of ECG signals captured at a point in time with a window of interest (WOI) time period around the reference annotations of the first set of ECG signals, the subset of signals each having a morphology pattern within the WOI;
storing the morphology patterns of the subset of ECG signals;
receiving continuous sets of ECG signals taken over a plurality of heartbeats of the human subject, the continuous sets of ECG signals being received over the plurality of channels, each of the continuous sets of ECG signals having a morphology pattern within a time period equal to the WOI time period for each heartbeat;
performing a correlation between the stored morphology patterns of the first set of ECG signals and the morphology patterns of each of the continuous sets of ECG signals for each heartbeat;
generating for each heartbeat of the plurality of heartbeats a correlation coefficient that is a measure of a goodness of fit between geometries of the first set of ECG signals and each of the continuous sets of ECG signals; and
identifying each heartbeat of the plurality of heartbeats having a correlation coefficient that exceeds a threshold coefficient as having been caused by an arrhythmia.

2. The method of claim 1, wherein the reference annotations correspond to a time of occurrence selected from the group consisting of a largest positive value on one selected ECG signal, a largest negative value on one selected ECG signal, a largest positive slope on one selected ECG signal and a largest negative slope on one selected ECG signal.

3. The method of claim 2, wherein the time of occurrence corresponds to a time of activation of a section of myocardium generating the ECG signals.

4. The method of claim 1, wherein a weighted correlation score is calculated over all the channels, for each heartbeat.

5. The method of claim 1, wherein a location of the identified heartbeat is incorporated into a map of the heart generating the ECG signals.

6. The method of claim 1, further comprising applying a phase shift between the first set of ECG signals and the continuous sets of ECG signals prior to generating the correlation coefficient.

7. The method of claim 6, further comprising iteratively altering the phase shift to determine a maximum weighted correlation coefficient, and identifying each heartbeat of the plurality of heartbeats having a maximum weighted correlation coefficient that exceeds the threshold coefficient as having been caused by an arrhythmia.

8. An apparatus, comprising:
a set of electrodes configured to be positioned in a heart of a human subject for acquiring electrocardiograph (ECG) signals over a plurality of channels; and
a processor, configured for:
processing a first set of electrocardiograph (ECG) signals taken over a single heartbeat of a human subject;
receiving reference annotations of the first set of ECG signals;
selecting a subset of the first set of ECG signals captured at a point in time with a window of interest (WOI) time period around the reference annotations of the first set of ECG signals, the subset of signals each having a morphology pattern within the WOI;
storing the morphology patterns of the subset of ECG signals;
receiving continuous sets of ECG signals taken over a plurality of heartbeats of the human subject, the continuous sets of ECG signals being received over the plurality of channels, each of the continuous sets of ECG signals having a morphology pattern within a time period equal to the WOI time period for each heartbeat;

performing a correlation between the stored morphology patterns of the first set of ECG signals and the morphology patterns of each of the continuous sets of ECG signals for each heartbeat;

generating for each heartbeat of the plurality of heartbeats a correlation coefficient that is a measure of a goodness of fit between geometries of the first set of ECG signals and each of the continuous sets of ECG signals; and identifying each heartbeat of the plurality of heartbeats having a correlation coefficient that exceeds a threshold coefficient as having been caused by an arrhythmia.

9. The apparatus of claim 8, wherein the reference annotations correspond to a time of occurrence selected from the group consisting of a largest positive value on one selected ECG signal, a largest negative value on one selected ECG signal, a largest positive slope on one selected ECG signal and a largest negative slope on one selected ECG signal.

10. The apparatus of claim 9, wherein the time of occurrence corresponds to a time of activation of a section of myocardium generating the ECG signals.

11. The apparatus of claim 8, wherein a weighted correlation score is calculated over all the channels, for each heartbeat.

12. The apparatus of claim 8, wherein a location of the identified heartbeat is incorporated into a map of the heart generating the ECG signals.

13. The apparatus of claim 8, further comprising applying a phase shift between the first set of ECG signals and the continuous sets of ECG signals prior to generating the correlation coefficient.

14. The apparatus of claim 13, further comprising iteratively altering the phase shift to determine a maximum weighted correlation coefficient, and identifying each heartbeat of the plurality of heartbeats having a maximum weighted correlation coefficient that exceeds the threshold coefficient as having been caused by an arrhythmia.

15. A computer program product comprising:
program instructions on a non-transitory computer-readable storage medium, where execution of the program instructions using a computer causes the computer to perform a method, comprising:
processing a first set of electrocardiograph (ECG) signals taken over a single heartbeat of a human subject, the first set of ECG signals being received over a plurality of channels;
receiving reference annotations of the first set of ECG signals;
selecting a subset of the first set of ECG signals captured at a point in time with a window of interest (WOI) time period around the reference annotations of the first set of ECG signals, the subset of signals each having a morphology pattern within the WOI; storing the morphology patterns of the subset of ECG signals;
receiving continuous sets of ECG signals taken over a plurality of heartbeats of the human subject, the continuous sets of ECG signals being received over the plurality of channels, each of the continuous sets of ECG signals having a morphology pattern within a time period equal to the WOI time period for each heartbeat;
performing a correlation between the stored morphology patterns of the first set of ECG signals and the morphology patterns of each of the continuous sets of ECG signals for each heartbeat;
generating for each heartbeat of the plurality of heartbeats a correlation coefficient that is a measure of a goodness of fit between geometries of the first set of ECG signals and each of the continuous sets of ECG signals; and
identifying each heartbeat of the plurality of heartbeats having a correlation coefficient that exceeds a threshold coefficient as having been caused by an arrhythmia.

16. The computer program product of claim 15, wherein the reference annotations correspond to a time of occurrence selected from the group consisting of a largest positive value on one selected ECG signal, a largest negative value on one selected ECG signal, a largest positive slope on one selected ECG signal and a largest negative slope on one selected ECG signal.

17. The computer program product of claim 16, wherein the time of occurrence corresponds to a time of activation of a section of myocardium generating the ECG signals.

18. The computer program product of claim 15, wherein a weighted correlation score is calculated over all the channels, for each heartbeat.

19. The computer program product of claim 15, wherein a location of the identified heartbeat is incorporated into a map of the heart generating the ECG signals.

20. The computer program product of claim 15, further comprising applying a phase shift between the first set of ECG signals and the continuous sets of ECG signals prior to generating the correlation coefficient and iteratively altering the phase shift to determine a maximum weighted correlation coefficient, and identifying each heartbeat of the plurality of heartbeats having a maximum weighted correlation coefficient that exceeds the threshold coefficient as having been caused by an arrhythmia.

* * * * *